United States Patent [19]
Bourzat et al.

[11] 4,185,107
[45] Jan. 22, 1980

[54] MEDICAMENTS CONTAINING A THIAZOLINE DERIVATIVE

[75] Inventors: Jean-Dominique Bourzat, Paris; Daniel Farge, Thiais; André Léger, Paris; Gerard Ponsinet, Sucy-en-Brie, all of France

[73] Assignee: Rhone-Poulenc Industries, Paris, France

[21] Appl. No.: 952,199

[22] Filed: Oct. 17, 1978

[30] Foreign Application Priority Data

Oct. 19, 1977 [FR] France .................. 77 31430

[51] Int. Cl.$^2$ ............................. A61K 31/44

[52] U.S. Cl. .................................. 424/263
[58] Field of Search ......................... 424/263

[56] References Cited

U.S. PATENT DOCUMENTS 3,723,125   3/1973   Hayashi et al. ................ 96/56.2

Primary Examiner—Frederick E. Waddell
Attorney, Agent, or Firm—Stevens, Davis, Miller & Mosher

[57] ABSTRACT

4-Methyl-3-(pyrid-2-yl)-$\Delta^4$-thiazoline-2-thione, a known compound, has been found to be useful as an anti-ulcer medicament.

5 Claims, No Drawings

MEDICAMENTS CONTAINING A THIAZOLINE DERIVATIVE

DESCRIPTION

This invention relates to the use of 4-methyl-3-(pyrid-2-yl)-$\Delta^4$-thiazoline-2-thione as a medicament and to pharmaceutical compositions containing it.

It has previously been disclosed in British Pat. No. 1,326,411 (Fuji Photo Film Co. Ltd.) and in corresponding U.S. Pat. No. 3,723,125 that 4-methyl-3-(pyrid-2-yl)-$\Delta^4$-thiazoline-2-thione of the formula:

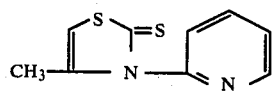   I is useful in the formation of colour photographic images.

It has now unexpectedly been found that 4-methyl-3-(pyrid-2-yl)-$\Delta^4$-thiazoline-2-thione is also useful as a medicament and, more particularly, as an anti-ulcer agent.

It has shown itself to be active as an anti-ulcer agent in guinea-pigs at a dose of about 25 mg/kg animal body weight, administered orally, according to the technique of Anderson and Watt, J. Physiol. (London), 147, 52 P (1959).

Its acute toxicity to mice is between 300 and 900 mg/kg animal body weight, administered orally.

The present invention therefore is concerned with pharmaceutical compositions comprising, as active ingredient, the thiazoline derivative of formula I in association with a pharmaceutically-acceptable carrier or coating. The invention includes especially such preparations made up for oral, parenteral or rectal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile suspensions or emulsions and non-aqueous solutions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised by, for example, filtration through a bacteria-retaining filter, by incorporation in the compositions of sterilising agents, by irradiation, or by heating. They may also be manufactured in the form of sterile solid compositions, which can be dissolved in a sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained.

In human therapy, the pharmaceutical compositions according to the invention are particularly useful in the treatment of various forms of gastritis and gastralgia, especially those caused by other medicaments, and in the treatment of ulcerous maladies (e.g. gastric or duodenal ulcers or peptic ulcers).

In human therapy, the doses of the thiazoline derivative depend on the desired effect and the duration of the treatment; adult doses are generally between 500 and 2500 mg per day, administered orally.

In general, the physician will decide the posology considered appropriate, taking into account the age and weight and other factors intrinsic to the patient being treated.

The following Example illustrates pharmaceutical compositions according to the present invention comprising 4-methyl-3-(pyrid-2-yl)-$\Delta^4$-thiazoline-2-thione.

EXAMPLE

Tablets having the following composition are prepared in accordance with the usual technique:

| | |
|---|---|
| 4-methyl-3-(pyrid-2-yl)-$\Delta^4$-thiazoline-2-thione | 250 mg |
| starch | 75 mg |
| precipitated silica | 47.5 mg |
| magnesium stearate | 2.5 mg |

4-Methyl-3-(pyrid-2-yl)-$\Delta^4$-thiazoline-2-thione can be prepared by reacting an $\alpha$-halogenoketone of the general formula:

$$CH_3COCH_2X \qquad\qquad II$$

(wherein X represents a halogen, preferably a bromine or chlorine, atom) with a dithiocarbamate of the general formula:

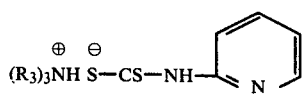   III (wherein each of the symbols $R_3$ represents an alkyl radical containing 1 to 4 carbon atoms, the alkyl radicals being the same or different), followed by dehydration of the thiazolidine obtained of the formula:

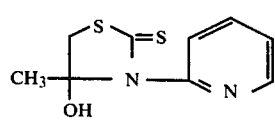   IV viz. 4-hydroxy-4-methyl-3-(pyrid-2-yl)-thiazolidine-2-thione, to the thiazoline derivative of formula I.

Generally the $\alpha$-halogenoketone of general formula II is reacted with the dithiocarbamate of general formula III in an organic solvent (e.g. dimethylformamide or acetonitrile), in water or in an aqueous-organic medium (e.g. water-acetonitrile), at a temperature between −10° and +50° C.

The dehydration of the intermediate of formula IV is advantageously carried out in a strong inorganic or organic acid medium at a temperature between 60° C. and the reflux temperature of the reaction mixture. Preferably the dehydration reaction is carried out in the presence of p-toluenesulphonic acid in an organic solvent such as toluene, or in the presence of a methanolic solution of hydrogen chloride. It is not essential to isolate the thiazolidine of the formula IV in order to carry out the dehydration.

The dithiocarbamates of general formula III can be obtained in accordance with the method described by E. B. Knott, J. Chem. Soc., 1644–9 (1956), or in accordance with German Patent Application DE No. 2,508,891 by the action of carbon disulphide on 2-aminopyridine in the presence of a tertiary amine.

The following Reference Example illustrates the preparation of the thiazoline derivative of formula I.

REFERENCE EXAMPLE

Chloroacetone (19.6 cc) is added, at 20° C., to a solution of triethylammonium pyrid-2-yldithiocarbamate (66 g) in dimethylformamide (300 cc). The reaction mixture is stirred for 1 hour at 20° C. The thiethylammonium chloride formed is removed by filtering the reaction mixture and is washed with dimethylformamide (50 cc).

After evaporating off the dimethylformamide under reduced pressure (0.1 mm Hg) at 50° C., the residual oil is taken up in methylene chloride (700 cc) and the solution thus obtained is washed twice with distilled water (total 200 cc), dried over sodium sulphate and evaporated to dryness under reduced pressure (20 mm Hg) at 20° C. The oily residue is crystallised from a mixture of diisopropyl ether (50 cc) and ethanol (50 cc). After cooling for 2 hours at 2° C., the crystals which have appeared are filtered off, washed twice with an ice-cooled mixture (20 cc in total) of ethanol (10 cc) and diisopropyl ether (10 cc) and dried under reduced pressure (20 mm Hg) at 20° C. The product obtained (50 g; m.p. 120° C.) is dissolved in boiling ethanol (80 cc), and diisopropyl ether (80 cc) and decolourising charcoal (1 g) are then added. After filtering the boiling solution and then cooling for 2 hours at 2° C., the resulting crystals are filtered off, washed twice with an ice-cooled mixture (20 cc in total) of ethanol (10 cc) and diisopropyl ether (10 cc) and dried under reduced pressure (0.1 mm Hg) at 20° C. 4-Hydroxy-4-methyl-3-(pyrid-2-yl)-thiazolidine-2-thione (37.1 g), melting at 122° C., is thus obtained.

A mixture comprising 4-hydroxy-4-methyl-3-(pyrid-2-yl)-thiazolidine-2-thione (9.05 g), toluene (100 cc) and p-toluenesulphonic acid monohydrate (1.0 g) is heated under reflux for 5 hours. The reaction mixture is then cooled to 20° C. and a 10% (w/v) aqueous solution of sodium bicarbonate (100 cc) is then added. The organic phase is decanted, washed with distilled water (250 cc), dried over sodium sulphate and evaporated to dryness under reduced pressure (20 mm Hg) at 40° C.

The product obtained (8.5 g) is dissolved in boiling ethanol (30 cc), and decolourising charcoal (0.2 g) is added. After filtering the boiling solution and then cooling for 2 hours at 2° C., the crystals which have appeared are filtered off, washed twice with ice-cooled ethanol (total 10 cc) and dried under reduced pressure (0.1 mm Hg) at 45° C. 4-Methyl-3-(pyrid-2-yl)-Δ⁴-thiazoline-2-thione (7.0 g), melting at 92° C., is thus obtained.

Triethylammonium pyrid-2-yldithiocarbamate is prepared in accordance with the method described by E. B. Knott, J. Chem. Soc., pages 1644–9 (1956).

We claim:

1. A pharmaceutical composition useful for the treatment of a patient with gastritis, gastralgia or an ulcerous malady, which comprises an effective amount for a said treatment of 4-methyl-3-(pyrid-2-yl)-Δ⁴-thiazoline-2-thione of the formula:

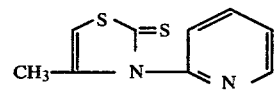

in association with a pharmaceutically-acceptable carrier.

2. A pharmaceutical composition according to claim 1 in a form suitable for oral, parenteral or rectal administration.

3. A pharmaceutical composition according to claim 1 in the form of tablets.

4. A method for the treatment of a patient with gastritis, gastralgia or an ulcerous malady which comprises administering orally, parenterally or rectally to the patient an effective amount of 4-methyl-3-(pyrid-2-yl)-Δ⁴-thiazoline-2-thione.

5. A method according to claim 4 in which an amount of from 500 to 2500 mg of 4-methyl-3-(pyrid-2-yl)-Δ⁴-thiazoline-2-thione is administered orally to an adult patient per day.